(12) United States Patent
Dhanantwari et al.

(10) Patent No.: US 11,257,261 B2
(45) Date of Patent: Feb. 22, 2022

(54) COMPUTED TOMOGRAPHY VISUALIZATION ADJUSTMENT

(71) Applicant: KONINKLIJKE PHILIPS N.V., Eindhoven (NL)

(72) Inventors: Amar Chandra Dhanantwari, Solon, OH (US); Gezheng Wen, Austin, TX (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 169 days.

(21) Appl. No.: 15/745,158

(22) PCT Filed: Jul. 1, 2016

(86) PCT No.: PCT/IB2016/053962
§ 371 (c)(1),
(2) Date: Jan. 16, 2018

(87) PCT Pub. No.: WO2017/013514
PCT Pub. Date: Jan. 26, 2017

(65) Prior Publication Data
US 2019/0012815 A1 Jan. 10, 2019

Related U.S. Application Data

(60) Provisional application No. 62/195,975, filed on Jul. 23, 2015.

(51) Int. Cl.
*G06T 11/00* (2006.01)
*A61B 6/03* (2006.01)
(Continued)

(52) U.S. Cl.
CPC ............ *G06T 11/008* (2013.01); *A61B 6/032* (2013.01); *A61B 6/461* (2013.01); *A61B 6/52* (2013.01);
(Continued)

(58) Field of Classification Search
CPC ......... G06T 11/008; G06T 5/009; G06T 5/40; G06T 5/50; A61B 6/032; A61B 6/461; A61B 6/52; A61B 6/5294
See application file for complete search history.

(56) References Cited

U.S. PATENT DOCUMENTS 5,305,204 A 4/1994 Ohhashi
5,357,549 A 10/1994 Maack
(Continued)

OTHER PUBLICATIONS

Ku, et al., "Virtual monochromatic imaging in dual-source dual-energy CT: radiation dose and image quality", Med Phys., vol. 38, No. 12, pp. 6371-6379, 2011.
(Continued)

*Primary Examiner* — Qun Shen
(74) *Attorney, Agent, or Firm* — Larry Liberchuk

(57) ABSTRACT

A computed tomography (CT) image display system (10) includes a mapping unit (32), which receives reconstructed volumetric image data (28) of a subject with values in Hounsfield Units (HU), and a set of reference settings (34), adjusts the set of reference settings (34) to an adjusted set of reference settings (35) according to a pixel-value distribution analysis of the HU values selected according to the reference settings (34), and maps the values in HU to gray scale values according to the adjusted reference settings (35).

14 Claims, 9 Drawing Sheets

(51) Int. Cl.
*A61B 6/00* (2006.01)
*G06T 5/40* (2006.01)
*G06T 5/00* (2006.01)
*G06T 5/50* (2006.01)

(52) U.S. Cl.
CPC ............ *A61B 6/5294* (2013.01); *G06T 5/009* (2013.01); *G06T 5/40* (2013.01); *G06T 5/50* (2013.01); *A61B 6/481* (2013.01); *G06T 2207/10081* (2013.01); *G06T 2207/20208* (2013.01); *G06T 2207/30008* (2013.01); *G06T 2211/40* (2013.01)

(56) References Cited

U.S. PATENT DOCUMENTS

| | | | |
|---|---|---|---|
| 5,900,732 A | 5/1999 | Felmlee | |
| 6,898,263 B2 | 5/2005 | Avinash | |
| 7,218,763 B2 | 5/2007 | Belykh | |
| 9,076,033 B1* | 7/2015 | Barron | G06F 3/04842 |
| 9,600,879 B2 | 3/2017 | Bystrov | |
| 9,747,700 B2 | 8/2017 | Smith | |
| 2003/0095696 A1* | 5/2003 | Reeves | G06T 7/0012 |
| | | | 382/131 |
| 2004/0064038 A1 | 4/2004 | Bruder | |
| 2004/0170308 A1 | 9/2004 | Belykh | |
| 2007/0047826 A1* | 3/2007 | Aritomi | H04N 1/00883 |
| | | | 382/232 |
| 2008/0050002 A1 | 2/2008 | Arnold | |
| 2009/0208078 A1* | 8/2009 | Fritz | G06T 7/0012 |
| | | | 382/130 |
| 2009/0296152 A1* | 12/2009 | Mestha | H04N 1/6033 |
| | | | 358/2.1 |
| 2010/0104160 A1 | 4/2010 | Lavi | |
| 2010/0130860 A1* | 5/2010 | Yamagata | A61B 8/13 |
| | | | 600/443 |
| 2010/0131885 A1 | 5/2010 | Licato | |
| 2011/0002523 A1 | 1/2011 | Prakash | |
| 2012/0223994 A1* | 9/2012 | Yuda | B41J 2/2132 |
| | | | 347/14 |
| 2013/0101189 A1* | 4/2013 | Robitaille | G06T 5/007 |
| | | | 382/128 |
| 2013/0198687 A1* | 8/2013 | Bird | A61B 5/7435 |
| | | | 715/810 |
| 2013/0343622 A1* | 12/2013 | Ruiz | G06T 11/008 |
| | | | 382/131 |
| 2014/0177803 A1* | 6/2014 | Stevens | G06T 5/009 |
| | | | 378/98 |
| 2014/0292328 A1* | 10/2014 | Brady-Kalnay | G01R 33/3614 |
| | | | 324/309 |
| 2016/0331337 A1* | 11/2016 | Ben-Haim | A61B 6/503 |

OTHER PUBLICATIONS

Pizer, et al., "Adaptive histogram equalization and its variations," Computer Vision, Graphics, and Image Processing., vol. 39, No. 3, pp. 355-368, 1987.

\* cited by examiner

COMPUTED TOMOGRAPHY VISUALIZATION ADJUSTMENT

CROSS REFERENCE TO RELATED APPLICATIONS

This application is the U.S. National Phase application under 35 U.S.C. § 371 of International Application No. PCT/IB2016/053962, filed Jul. 1, 2016, published as WO 2017/013514 on Jan. 26, 2017, which claims the benefit of U.S. Provisional Patent Application No. 62/195,975 filed Jul. 23, 2015. These applications are hereby incorporated by reference herein.

FIELD OF THE INVENTION

The following generally relates to X-ray computed tomography (CT), and is described with particular application to visualization settings of displayed CT images and displayed CT multi-energy or spectral images.

BACKGROUND OF THE INVENTION

In CT imaging, X-rays from a radiation source pass through a volume of a subject or object and are detected by detectors. The energies of the X-rays are emitted in a distribution with a peak energy according to a CT imaging device and a set of imaging parameters, e.g. imaging protocol. The detected X-ray radiation, in the form of projection data, is reconstructed into volumetric image data, which can be presented as image slices or other divisions of the volume. The volumetric image data is reconstructed with voxel values in Hounsfield Units (HU). The range of Hounsfield Units is approximately from −1000 to 3000, e.g. range of 4096 values or 12-bit, which are based on measures of attenuation normalized with water at zero. A visualization of the volumetric image occurs on a display device or film, and is typically rendered in gray scale, which typically ranges from 0-255, e.g. 8-bit grayscale, at the limits of a healthcare practitioner's ability to discern differences in rendered pixels with gray scale values.

Reference settings are typically based on the type of imaging protocol selected for the imaging procedure. For example, a healthcare practitioner selects a CT imaging procedure for vasculature structure in the chest region. The acquisition parameters, such as the tube potential or emitted peak energy (kVp) are set based on the tissue and the region, e.g. 120 kVp. Higher energy levels are used for greater attenuation with larger patients or with more dense tissues, such as bone. The projection data is acquired with the acquisition parameters, and volumetric image data is reconstructed. Bone is represented from approximately 700 to 3000 in HU values. Reference settings, which can be site and/or healthcare practitioner specific are based on a selection of HU values which contrast the bone in the chest region, such as 800-1200. The selected range is mapped to the gray scale according to the reference settings, e.g. mapping of 800-1200 HU to 0-255 gray scale. Views of the volumetric image data are displayed using the reference settings.

The volumetric image data can be depicted at different x-ray energies, either by physically changing the x-ray peak energy, or by recasting the volumetric data to virtual energies. The volumetric image data at different energy levels is typically displayed using the same reference settings of a window level (WL), e.g. mean/median of selected HU values, and a window width (WW), e.g. the selected range of HU values. Displayed views of images at the different energy levels are different in gray scale renderings, which makes comparisons of the same tissues between the different images difficult to associate, e.g. liver tissue binned at 50 keV with liver tissue binned at 70 keV. Healthcare practitioners typically try to compensate by adjusting manually the display device brightness and/or contrast of the gray scale values between the changes in energy selection, which does not vary the underlying selected range of HU values.

Imaging parameters can change during imaging of a subject. For example, the emitted peak energy can be lower during imaging of lungs or abdomen, but increased in denser regions such as the chest or pelvic regions, e.g. kVp modulation. As the acquisition parameters change, the appearance of tissue can change. For example, with the emitted peak energy changing from one sub-volume or slice of liver tissue to another, the liver tissue can darken between slices. This change in appearance makes comparisons and/or identifying abnormalities difficult. Healthcare practitioners would need to compensate by adjusting manually the display device brightness and/or contrast of the gray scale values between the changes in image slices, which does not vary the underlying selected range of HU values.

With spectral CT or multi-energy CT, the distribution of HUs can include a large range and a bi-modal or multi-modal distribution. The bi-modal distribution reflects tissue and hightlighted or contrasted different materials, such as iodine, calcium, and the like. In a mapping of a large distribution, e.g. large WW, the precision and/or differentiation of tissues around the bi-modal peaks are reduced. For example, in a spectral image with iodine contrast, the iodine contrasted material peak is around 1200 HU while another non-iodine peak is around 200 HU, and a total range includes 50 to 1650 HU. Thus, the range of 1600 HUs are mapped to 256 gray scale values, which is more than a six fold narrowing of the distributions of values around each peak in a linear mapping. Tissues which are distinguished in the HU distribution of values, may not be readily distinguished in the gray scale values, which makes viewing and diagnosing based on the images difficult and hence is not common practice.

Comparing images acquired with different acquisition or recasting parameters for the same tissue can make the comparison more difficult. For example, comparing an image of one subject with other images of different subjects with normal tissues and/or abnormal or diseased tissues in the same anatomical region acquired with different energy levels, a consistency in gray scale rendering of like tissues would be advantageous.

SUMMARY OF THE INVENTION

Aspects described herein address the above-referenced problems and others.

The following describes an apparatus and method for adjusting visualization settings of a volumetric image from reference settings. The adjustment of the visualization settings is made based on a pixel-value distribution analysis of the underlying HU values according to the reference settings. The adjustment with CT spectral images can be made using a mask to selectively map HU values to gray scale values.

In one aspect, a computed tomography (CT) image display system includes a mapping unit, which receives reconstructed volumetric image data of a subject with values in Hounsfield Units (HU), and a set of reference settings, adjusts the set of reference settings to an adjusted set of reference settings according to a pixel-value distribution analysis of the HU values selected according to the reference settings, and maps the values in HU to gray scale values according to the adjusted reference settings.

In another aspect, a method of adjusting computed tomography (CT) visualization settings includes mapping Hounsfield Unit (HU) values of voxels, according to adjusted reference settings to gray scale values for a received reconstructed volumetric image data of a subject. The adjusted reference settings are determined from a pixel-value distribution analysis of HU values selected from the received reconstructed volumetric image data according to selected reference settings.

In another aspect, a spectral computed tomography (CT) image display system includes a mapping unit which receives a reconstructed volumetric image of a subject with values in Hounsfield Units (HU), generates a mask, based on a material specific image corresponding to the reconstructed volumetric image, and maps according to a selected reference settings the HU values of the reconstructed volumetric image which pass through the mask to gray scale values.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
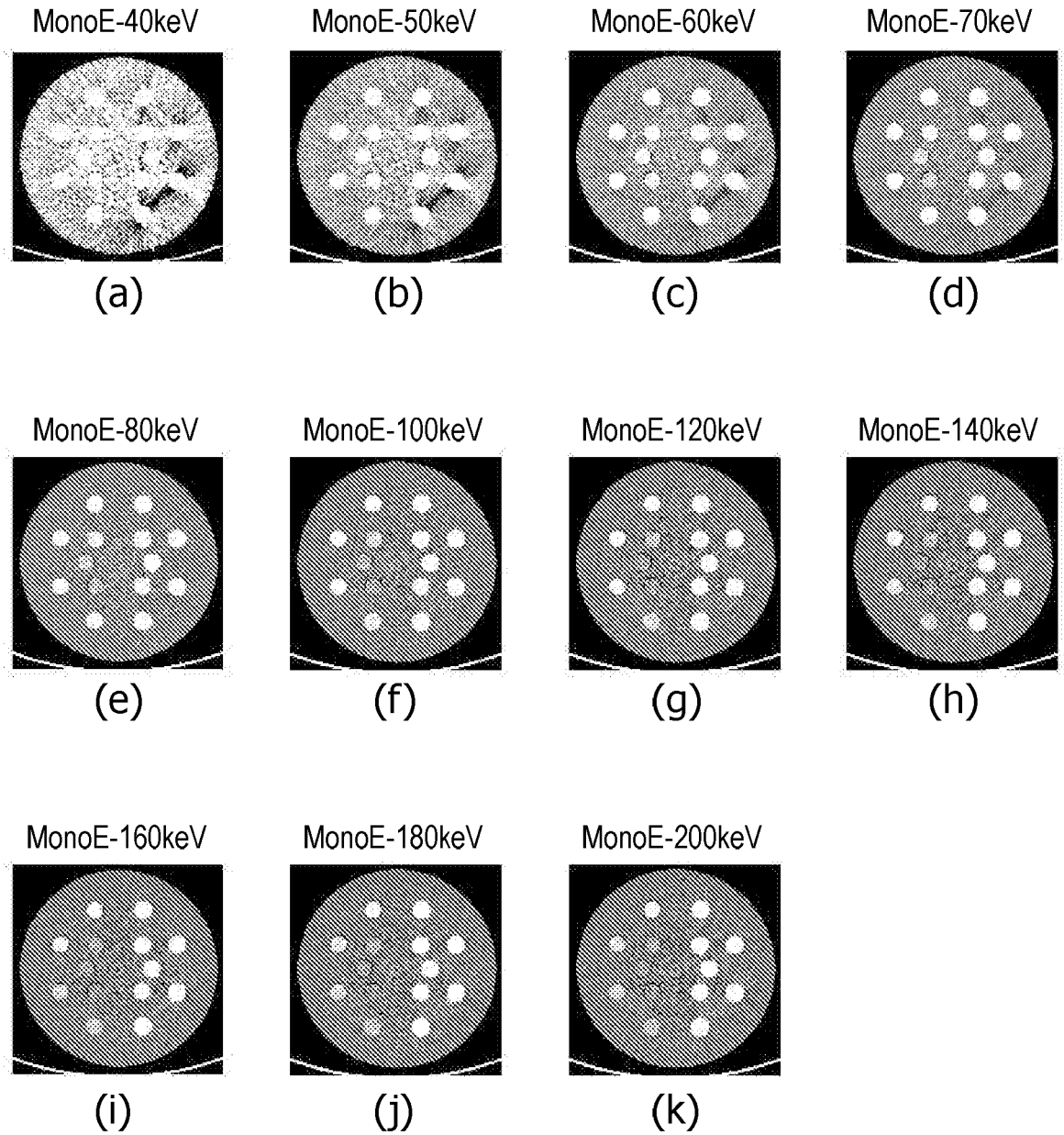
FIG. 1 illustrates exemplary CT images of a same phantom with different monochromatic energy levels and corresponding histograms of pixel values of a mapped gray scale using a fixed window level (WL) and window width (WW) of HU values.
Figure 1:
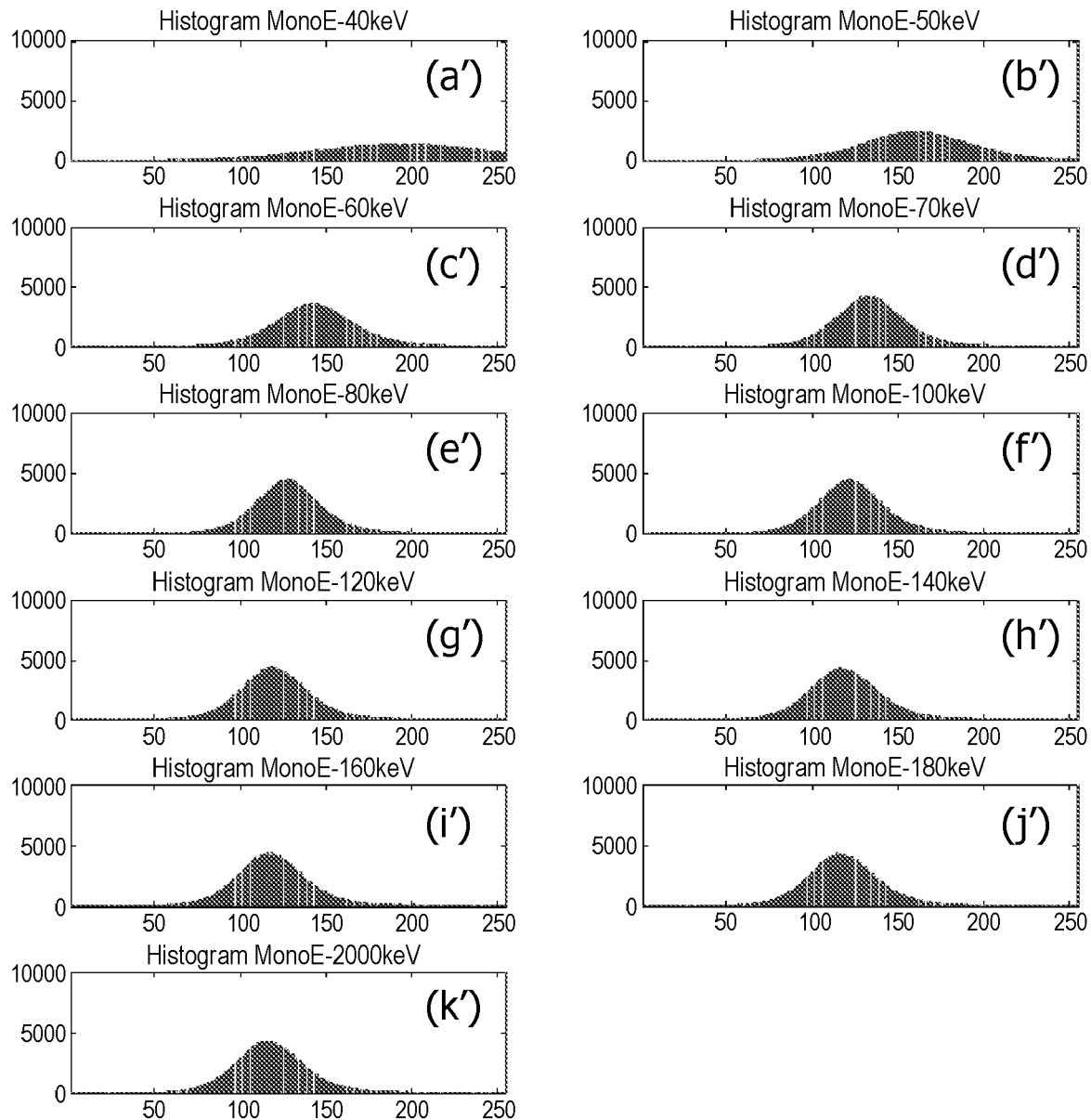

Initially referring to FIG. 1, example images of a same phantom are shown with monochromatic energy levels of 40, 50, 60, 70, 80, 100, 120, 140, 160, 180 and 200 keV (a)-(k). The displayed Monochromatic Energy (MonoE) images are linearly mapped from synthesized reconstructed image data with reference settings of a window level (WL) of 0 HU to a fixed gray scale of 128, and from a window width (WW) of 200 HU, e.g. −100 to +100 HU, to 0-255 gray scale values. The examples provide an indication of the image visualization according to the reference settings.

MonoE synthesized images are synthesized by scanning an object at multiple energies. For example, dual-energy or spectral scanning includes two energies and photon counting CT scanners can include greater numbers of energy levels. The detected multi-energy projection data is used to identify the material at each voxel by two or more x-ray attenuation components by decomposition. The x-ray attenuation components can include pairs of components, such as photoelectric properties and Compton scatter properties, aluminum likeness and water likeness, soft tissue likeness and bone likeness, and the like, which can include greater numbers of components with more energy levels, e.g. at two energy levels a maximum of three components can be identified. MonoE images are synthesized by casting these components with known interaction with x-ray of a corresponding energy level. For example, in spectral projection data, an aluminum likeness image and water likeness image are obtained from decomposing aluminum likeness and water likeness at each voxel. A MonoE image at 65 keV is obtained by multiplying the aluminum likeness image with known attenuation of aluminum at 65 keV and summing with the water likeness image multiplied with known attenuation of water at 65 keV.

Distributions of HU pixel-values mapped to gray scale values are shown as a histogram of gray scale values (a')-(k') corresponding to each example image. The horizontal axis of each histogram is in gray scale and the vertical axis is a count of the voxels in the image with the gray scale value. An analysis of the pixel-value distributions between the different energy levels illustrates the underlying cause of the variations in the gray scale images due to variations in distributions of HU values in the source of the mapping according to the reference values. This can occur due to energy modulation within reconstructed volumetric image data, between two reconstructed volumetric image data with different energies, and between volumetric image data at energy levels.

For example, in the 40 keV MonoE image materials or tissues are broadly differentiated in the displayed image as indicated by the distribution of values in the corresponding histogram. The histogram with gray scale values on the horizontal axis and voxel count on the vertical axis indicates the peak of the distribution is approximately 200 gray scale with a long tail to lower values and a truncated tail to higher values. The 50 keV histogram shows a shift in the mean gray scale values and a narrowing of the histogram peak from the 40 keV histogram, which continues progressively in the 60 keV and in the 70 keV histograms.

In one embodiment, the system records changes in imaging parameters according to a portion of the volumetric image, e.g. change in energy modulation by image sub-volume or slice(s). The change in imaging parameters for energy modulation can include a change in tube current, tube potential, peak energy level, mean energy level and the like. In another embodiment, the system depicts the volumetric image data at different energy levels.

Figure 2:
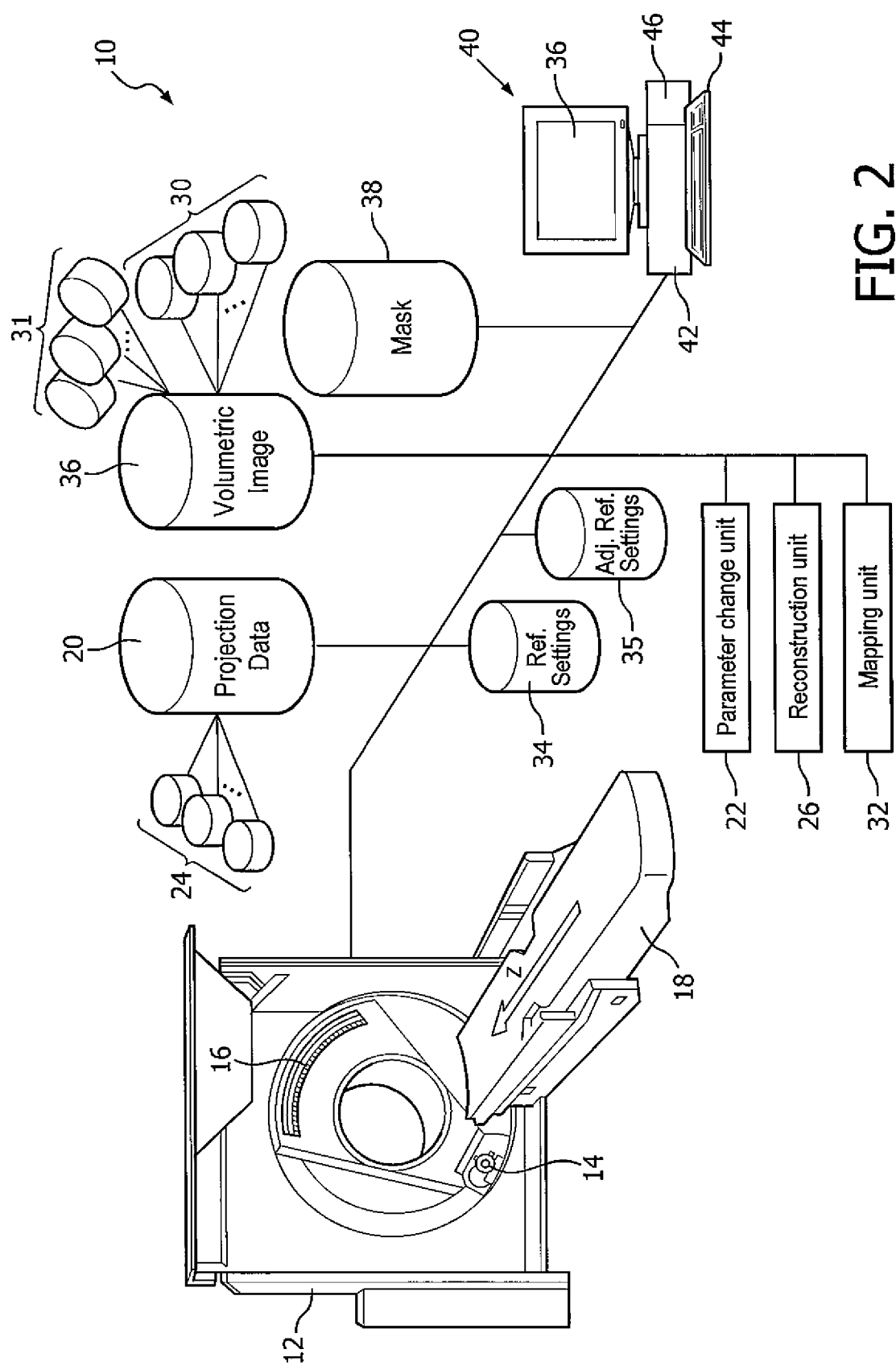
FIG. 2 schematically illustrates an embodiment of a CT system with adjustment of visualization settings.

With reference to FIG. 2, an embodiment of a CT system 10 with adjustment of visualization settings is illustrated. The CT system 10 includes a CT imaging device 12, which includes an energy source 14, such as an X-ray tube, and a detector array 16. The energy source 14 emits X-ray radiation with different peak energies. In one embodiment, the energy source 14 is a multi-energy source or CT spectral energy source. The CT imaging device 12 includes a subject support 18, which moves the subject along an axis relative to an imaging region defined by a volume between the energy source 14 and the detector array 16. As volumes of the subject pass between the energy source and the detector array 16, energies of the emitted X-rays traversing the volume of the subject are detected by the detector array 16, and stored as projection data 20.

As the imaging parameters change according to the imaging procedure, e.g. change in energies of the emitted X-rays based on anatomical region of subject, a parameter change unit 22 can record the change in imaging parameters with the corresponding sub-volume 24 of projection data 20. For example, as the peak energy (kVp) is changed at the energy source 14, the corresponding volume of projection data is tagged or labeled with the changed peak energy.

A reconstruction unit 26 reconstructs the projection data 20 into volumetric image data 28 using known CT reconstruction techniques. The volumetric image data 28 includes a plurality of image data 30, 31. In one embodiment, the reconstruction unit 26 can identify the corresponding image sub-volumes 30 according to the tagged projection data 20. The tags can include the changed parameters, such as the corresponding kVp, an indicator or pointer of positional change according to a protocol, and the like. The tags can be stored in the image metadata or stored separately. In one embodiment, the reconstruction can decompose the projection date 20 or volumetric image data 28 and depict image data synthesized as MonoE image data 31.

A mapping unit 32 maps HUs of the volumetric image data 28 voxels to gray scale values according to a reference settings 34, and the references settings are adjusted according to a pixel-value distribution analysis of the volumetric image data 28. The adjustment can be by each tagged reconstructed sub-volume 30, and/or other volumetric image data which differ by energy level. The adjustment can be by each energy level of MonoE image data 31. In one embodiment, the mapping unit 32 maps the HUs of each MonoE image data 31 in parallel.

The pixel-value distribution analysis identifies adjust reference settings 35 which include an adjusted WL and/or adjusted WW, and are based on the HU values in the reference range, such as a mean, median, weighted mean, weight median, standard deviation, quantile, kurtosis, skewness, and the like. For example, a median value of the HU values selected according to the reference settings is computed as the adjusted WL. In another example, a function of a variance of the distribution of HU values selected according to the reference settings is computed as an adjusted WW. A mapping can be applied based on the pixel-value distribution analysis selected according to the analysis, which can be a linear and/or non-linear mapping using known techniques.

The volumetric image data 28, one of the sub-volumes 30, and/or MonoE image data 31 at one energy level, as mapped to gray scale values with the adjusted settings, are displayed on a display device 36. In some instances, the mappings provide consistency across changing imaging parameters; the same tissue appears with the same gray scale values across sub-volumes generated with different energies, e.g. modulated and/or synthesized. The mapping can include the creation of a mask 38, which removes, eliminates, weakens or minimizes voxels of the masked material from the volumetric image data, sub-volumes 30, and/or MonoE image data 31 at synthesized energy levels in the mapping to the gray scale display. The HU values of the voxels of masked material is then applied in a second mapping to the gray scale display according to the reference settings 34 of the material HU range, which can also be adjusted based on a pixel-value distribution analysis. In some instances, the use of the mask improves the visual characteristics of the gray scale displayed image, which provide healthcare practitioners improved tissue differentiation and consistency of tissue rendering of CT spectral images.

The reference settings 34 include gray scale mappings according to an imaging protocol. The reference settings 34 can be customizable to a site or individual healthcare practitioner. The gray scale mappings of the reference settings 34 include at least one WL and WW. For multi-energy imaging, such as contrast agents, the reference settings can include additional WL and WW values. For example, the rendering of a renal volumetric image data with an iodine contrast includes a first reference WL and WW of non-contrasted tissue and a second reference WL and WW of contrasted tissue according to an imaging protocol, e.g. according to energies used to acquire data in an anatomical region. The imaging protocol can include a set of imaging parameters according to subject characteristics, such as weight, gender, age, and the like, which can change the energies used during acquisition.

The mappings of each MonoE image data 31, tagged sub-volume 30, the volumetric image 28 with applied mask 38, sub-volumes 30 with applied mask 38, or the applied masked material can include a linear or non-linear mapping. The linear or non-linear mapping can include change with respect to bias, gain or shift. For example, bias (b), gain (g), and shift (s) control the shape of a rescaling curve of the mapping, where b and g are constant scalars defined in the range of [0, 1], and s is a pair of scalars representing the location of the gain point in the grid (i.e., $s=(s_x, s_y)$). Given a specific chosen adjusted WL and adjusted WW, the HU numbers of the volumetric image with mask or sub-volume can be normalized into the range of [0, 1], and such normalized HU number is denoted as t. The rescaled normalized HU number Y in the range of [0, 1], as a function of b, g and s at each t are defined as:

$$\beta_b(t) = \frac{t}{\left(\frac{1}{b} - 2\right)(1-t) + 1}, \beta_g(t) = \frac{t}{\left(\frac{1}{g} - 2\right)(1-t) + 1}$$

$$\gamma_{b,s,g}(t) = \begin{cases} s_y \times \beta_g\left(\frac{\beta_b(t)}{s_x}\right): & \beta_b(t) < s_x \\ 1 - (1 - s_y) \times \beta_g\left(\frac{1 - \beta_b(t)}{1 - s_x}\right): & \beta_b(t) \geq s_x \end{cases}$$

After multiplying the normalized HU number Y by 255, the dynamic range of HU numbers is mapped into the display range of 256 gray scale values. Other known linear or non-linear mapping techniques can be used for the mappings.

The display device 36 can comprise a computing device 40, such as a workstation, laptop, tablet, smart phone, body worn computing device, server, and the like. The computing device includes a processor 42, such a digital processor, microprocessor, electronic processor, optical processor, multi-processor, and the like. The computing device includes one or more input devices 44, such as a keyboard, mouse, microphone, touch screen, and the like. The input device 44 can be used to navigate the mapped volumetric image 28, mapped sub-volumes 30, and/or selecting or customizing the reference image.

The volumetric image 28 includes at least a three-dimensional (3D) image, e.g. volume image comprising 2D slices, 3D image, 4D image, etc. The volumetric image 28 can be received directly from the CT imaging device 12 or stored in an electronic memory, such as a Picture Archiving and Communication System (PACS), a Radiology Information System (RIS), an Electronic Medical Record (EMR), cloud storage, server storage, local storage, and the like. The reference settings 34 are stored in an electronic memory.

The parameter change unit 22, the reconstruction unit 26, and the mapping unit 128 are suitably embodied by one or more configured processors, such as the processor 42, a distribution of processors include peer-to-peer or cooperatively operating processors, client-server arrangement of processors, and the like. The configured processor executes at least one computer readable instruction stored in a computer readable storage medium ("memory") 46, which excludes transitory medium and includes physical memory and/or other non-transitory medium to perform the disclosed parameter change recording, reconstruction, pixel-value distribution analysis and mapping techniques. The configured processor may also execute one or more computer readable instructions carried by a carrier wave, a signal or other transitory medium.

Figure 3:
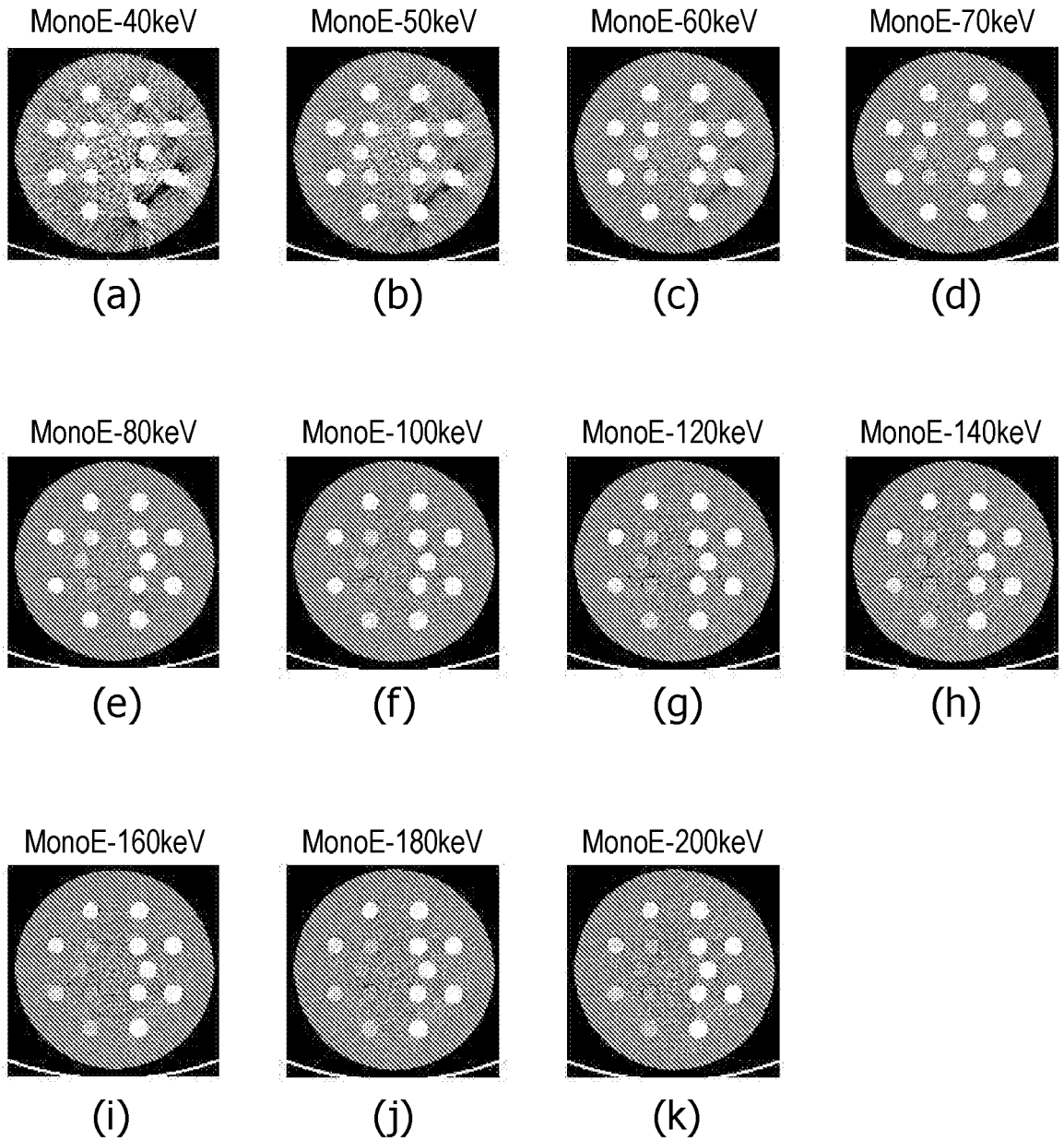
FIG. 3 illustrates exemplary CT images of the same phantom with different energy levels and corresponding histograms of mapped gray scale pixel values with adjusted visualization settings.
Figure 3:
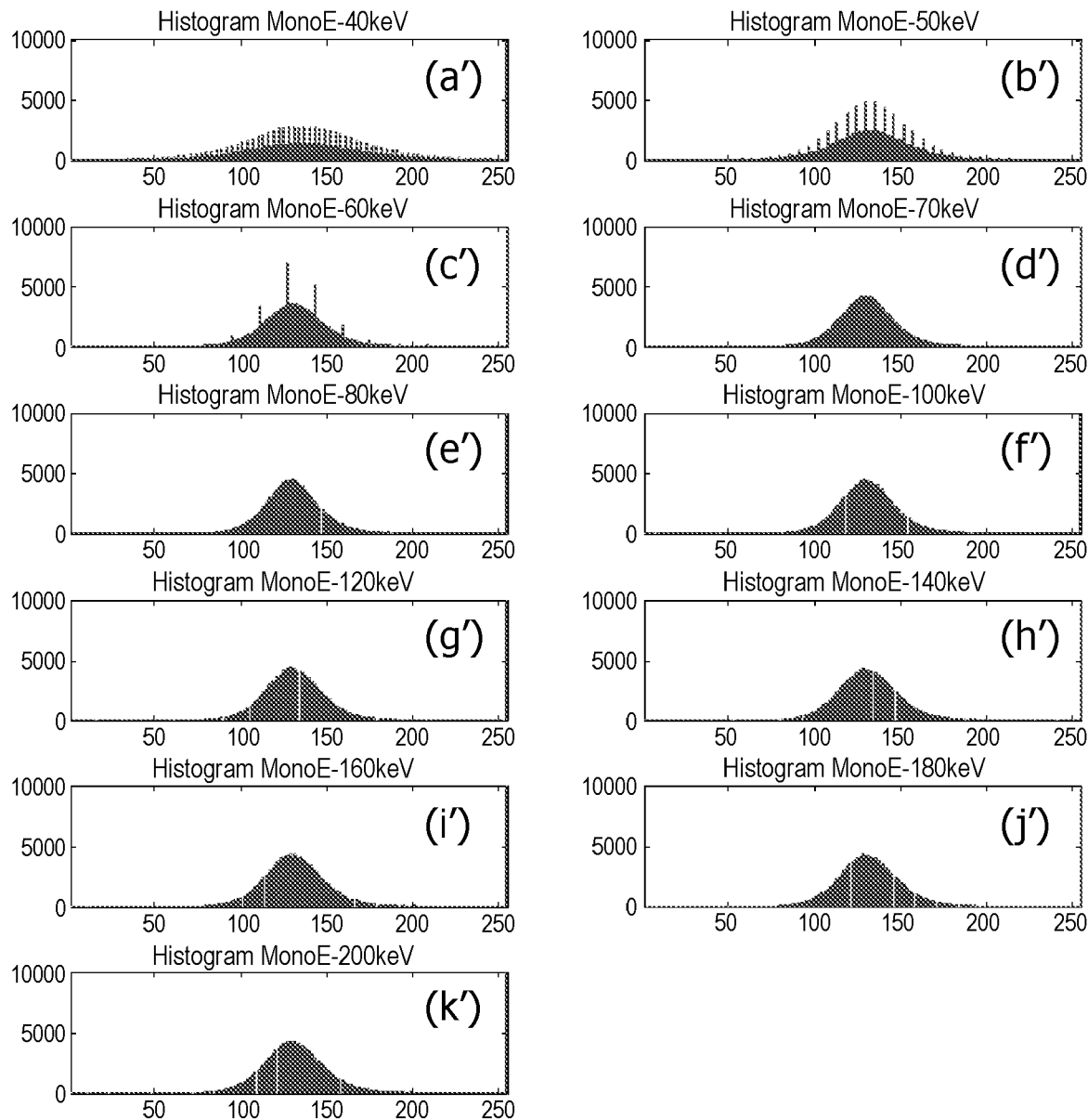

With reference to FIG. 3, exemplary CT images of the same phantom synthesized at different energy levels, the same energies (a)-(k) as FIG. 1 and corresponding histograms (a')-(k') of mapped gray scale pixel values with adjusted visualization settings are illustrated. The example image slices use the same reconstructed images of the same phantom as described with reference to FIG. 1. The mappings to gray scale are different in the displayed images in FIG. 3. The mappings use an adjusted WL for each tagged sub-volume, MonoE image data or other volumetric image data at a different energy level. In the example the adjust WL is a mean of the corresponding voxel HU values selected according to the reference settings. For example, the mean value of the voxel HU values for of the synthesized image data at 40 keV selected according to the reference settings is mapped to the mean gray scale value for the display of the 40 keV image. The mean value of the voxel HU values of the synthesized image data at 50 keV selected according to the reference settings is mapped to the mean gray scale value for the display of the 50 keV image.

The mapping uses a function of the WW for each MonoE image data, which is a function of the standard deviation of the HU values selected according to the reference settings, such as 0.5*standard deviation. The WW varies by energy level of each synthesized image data energy level. The distribution of the 40 keV histogram shows a mean with evenly distributed tails of pixel values in contrast to the distribution of the 40 keV histogram shown and described in reference to FIG. 1. As shown, comparisons between the images of FIG. 3 are more easily made than in FIG. 1 with respect to discovery of differences due to physical changes in the underlying tissues, rather than the display characteristics of the gray scale mapping. Each tagged sub-volume or MonoE image data is independently mapped according to the reference settings.

Figure 4:
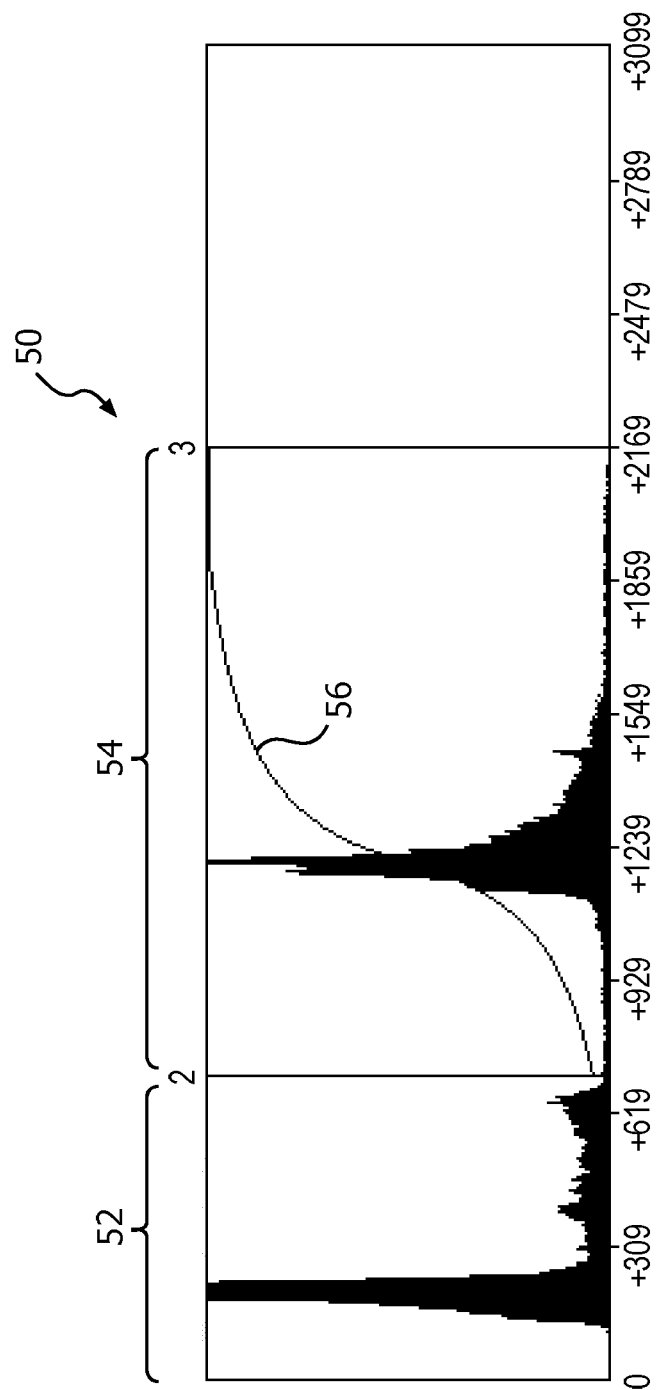
FIG. 4 illustrates an exemplary histogram of a CT spectral image voxel HU values, which include an iodine contrast with a superimposed non-linear mapping of masked material.

With reference to FIG. 4, an exemplary histogram of a CT spectral image with iodine contrast and a superimposed non-linear mapping of a masked material are illustrated. The example histogram 50 of pixel or voxel values in HU on the horizontal axis and the count of voxels on the vertical axis is based on volumetric image data with an iodine contrast agent. In a first range 52 including a first histogram peak, HU values represent non-iodine contrast, e.g. from approximately 100 to 700 HU. In a second range 54 including a second histogram peak, HU values represent iodine contrasted tissue, e.g. from approximately 700 to 2169 HU.

The mapping unit 32 generates a material specific mask, e.g. iodine material, based on the voxels in the second range 54, removes the iodine contrast voxels or pixels from the pixel-value distribution, and uses the remaining values selected according to reference settings in pixel-value distribution represented by values in the first range 52, e.g. the remaining WW extends from approximately 100 to 700 HU. The mapping unit 32 maps the first range to the gray scale without the iodine contrast tissues, e.g. with mask applied, as described in reference to FIGS. 2-3. The mapping unit 32 maps voxels or pixels in the second range 54 to gray scale using a second mapping 56. The second mapping of the iodine contrasted voxels includes a non-linear curve visually superimposed on the histogram, e.g. change in gain based on shape of curve and shift based on a change in mean value of second range relative to first range in the second mapping.

Figure 5A:
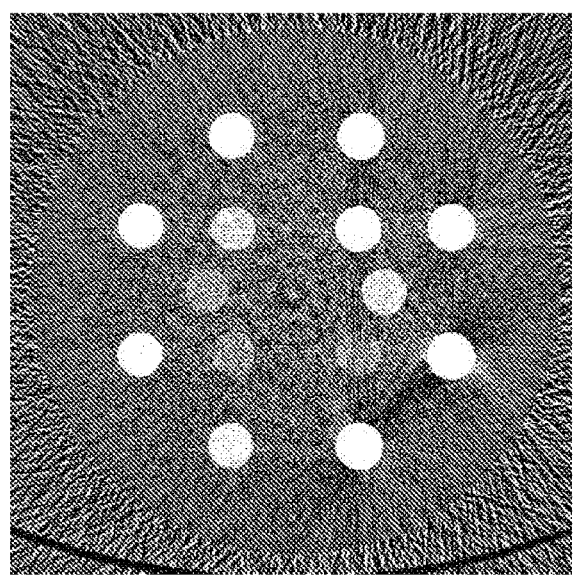
FIGS. 5A-5C illustrate exemplary output of mask development steps using the phantom.
Figure 5B:
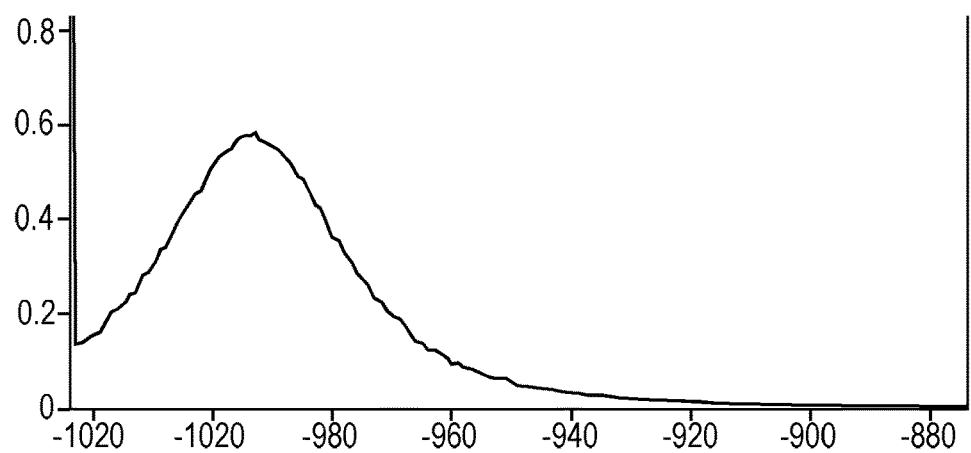
Figure 5C:
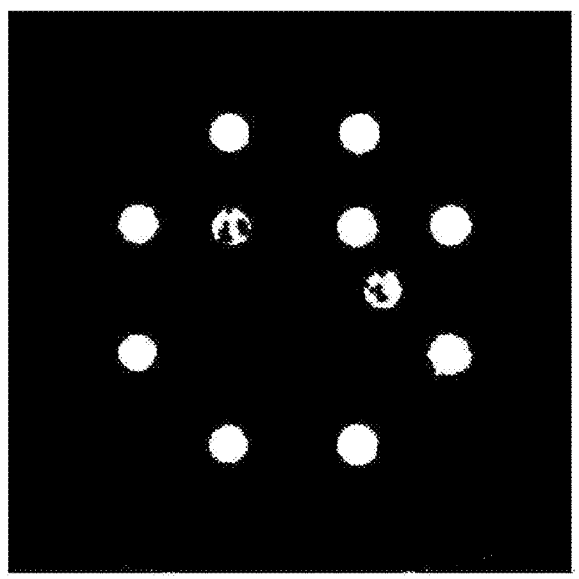

With reference to FIGS. 5A-5C, exemplary outputs of mask development steps using the same phantom are illustrated. A material specific image is generated from either of the volumetric image data 28, one of the sub-volumes 30 or one of the MonoE image data 31, such as an iodine_no_water image, an iodine_no_calcium image, and the like. The material specific image is generated through known material decomposition processes in spectral CT. FIG. 5A illustrates an iodine_no_water image of the phantom. A histogram of the pixel-value distribution can be generated by the mapping unit 32 as illustrated in FIG. 5B, in which the material specific voxel HUs are identified. The HU values are represented on the horizontal axis and the voxel count is represented on the vertical axis. The voxels with HU values in the range are designated as masked values, e.g. containing the material to be masked. The voxels with masked values comprise a mask, such as a binary mask, which is illustrated in FIG. 5C. The portions which are displayed dark are non-masked voxels, and the portions that are displayed in white are masked voxels.

The mask can be applied to the corresponding volume, which includes any one of the volumetric image data 28, one or more sub-volume 30 and/or one or more MonoE image data 31. The mapping unit 32, in obtaining the HU values for voxels to be mapped, applies the mask 38, through which non-masked voxels pass and are used in the first mapping of HU values to gray scale values, e.g. reference and adjusted WL and WW based on the voxels which pass through the mask. The mask can be inverted to identify the masked voxels for the second mapping, e.g. mapping of the material specific voxels. In some instances, the mask provides an efficient computing process with a binary multiplication operation to obtain the reference and/or adjusted WW and WL.

In one embodiment, the mask includes a soft mask, which includes values in the range of [0,1] as an alternative to the binary mask which includes only values of zero and one. The soft mask minimizes the masked values which pass through the mask in a first mapping. In the second mapping, the inverted mask can be used as a binary mask or to maximize the masked values in the second mapping or minimize the originally un-masked values in the second mapping.

Figure 6A:
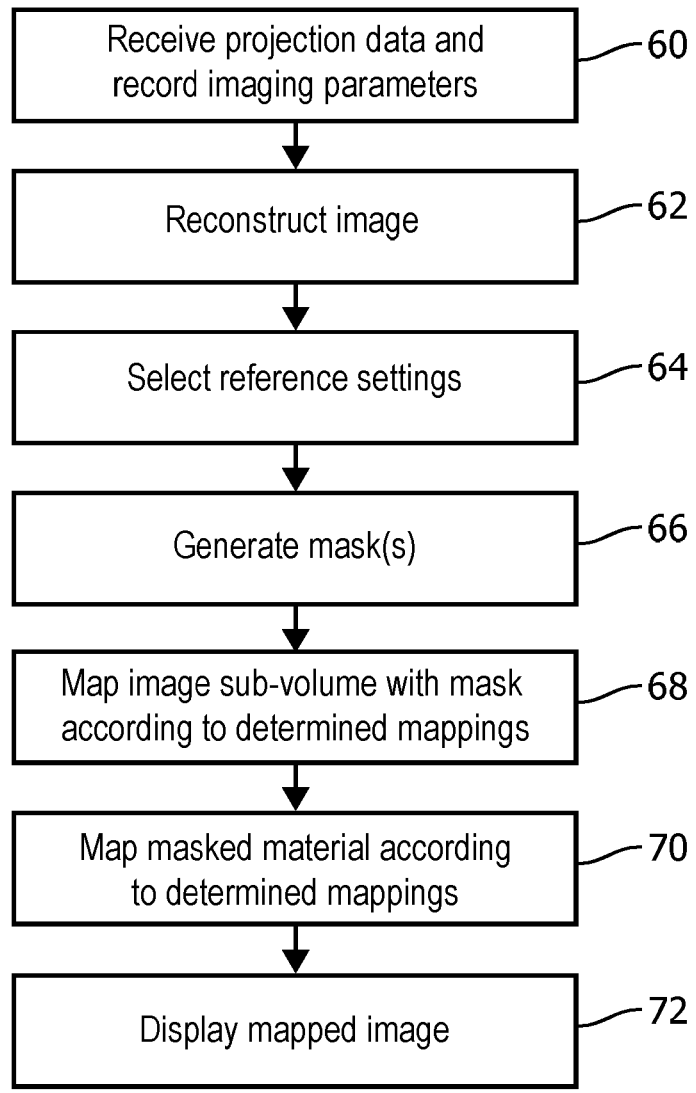
FIG. 6A-6C illustrate embodiments of adjusting visualization settings.

With reference to FIG. 6A, an embodiment of adjusting visualization settings of a CT spectral image is illustrated. At 60, spectral projection data 20 of a subject can be received from the detector array 16 and a parameter change unit 22 can record corresponding imaging parameters, which are different by sub-volume 24, e.g. modulated energy. The receiving and recording is repeated for each sub-volume 24.

At 62, volumetric image data 28 and a material specific image can be reconstructed by the reconstruction unit 26 from the spectral projection data and can include tagged sub-volumes 30, e.g. image slices comprising the volumetric image labeled according to imaging parameter changes. In one embodiment, the volumetric image data or tagged sub-volumes are synthesized by energy level.

The reference settings 34 are received at 64. A selection of the reference settings 34 can be received from the input device 44 and/or as part of other operational information for the CT imaging device 12, such as user login or healthcare practitioner identity, imaging protocol selection, patient information, and the like.

At 66, a mask 38 is generated for the volumetric image data 28, each tagged sub-volume 30 or each MonoE image data 31 based on the reconstructed material specific image(s) by the mapping unit 32. The mask can be constructed as one mask for the volumetric image data 28 or as individual masks for each tagged sub-volume 30 or MonoE image data 31. Each mask is a binary mask, which limits the voxels in the volumetric image data 28, sub-volume or MonoE image data HU values analyzed for adjusted reference settings 35 and mapped in a first mapping to gray scale values.

At 68, each tagged sub-volume or MonoE image data is mapped using a corresponding generated mask according to the adjusted reference settings 35. For example, slices in a lower lung region, e.g. a first sub-volume, are mapped according to a first set of adjusted reference settings using a first mask of iodine_no_calcium mask. Slices in an upper lung/cardiac region, e.g. a second sub-volume, are mapped according to a second set of adjusted reference settings using a second mask of iodine_no_calcium. Each mapping includes a linear or non-linear transform of HU voxel values to gray scale values according to the adjusted reference settings 35.

At 70, the masked material is mapped according to the selected reference settings adjusted for the sub-volume or MonoE image data. For example, the HU values of masked voxels in the lower lung region slices are mapped to the gray scale values according to the second set of adjusted reference settings. The second mapping can be mapped to adjacent gray scale values and/or overlap with the first mapping. The second mapping is performed for each sub-volume or MonoE image data according to the mask construction, e.g. each mask individually mapped using adjusted reference settings.

The one or more mapped sub-volumes, mapped MonoE image data and/or portions of the mapped volume are displayed on the display device 36 at 72. The position and/or orientation of the mapped volume can be determined by commands received from the input device 44. For example, a first slice of the lower lung is displayed on the display device. The slices can be stepped through using a mouse scroll. In some instances, as the display transitions from slices in the lower lung to the upper lung, the mapping keeps the gray scale values visually consistent between the lung tissue even through the imaging parameters, such as the peak energy changed. Moreover, the tissues contrasted by the contrast agent appear consistent between image slices. In another example, a frontal view is displayed, which uses portions of the volume obtained from multiple slices. In some instances, the tissues including the contrasted tissue appear consistent across the frontal view even through different portions may have different mappings according to the sub-volume orientation with respect to the view plane. In another example, a mapped 40 keV image is displayed of the lung region, which is compared with a 120 keV image of the same region, each mapped with different adjusted reference settings.

Figure 6B:
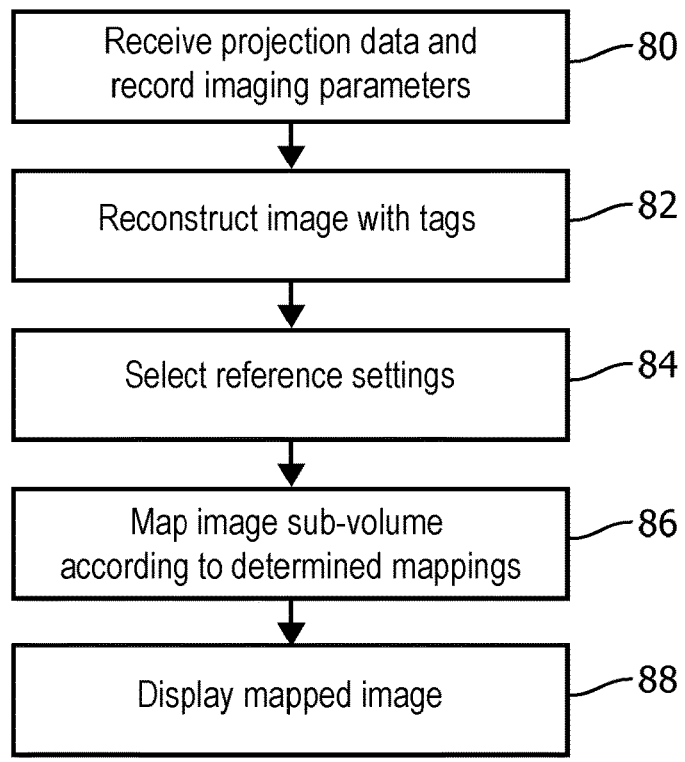

With reference to FIG. 6B, an embodiment of adjusting visualization settings of a CT image is illustrated, such as between two reconstructed volumetric image data at different energies, different sub-volumes at different modulated energies, e.g. change in imaging parameters during acquisition, or between MonoE images. At 60, CT projection data 20 of a subject can be received from the detector array 16 and a parameter change unit 22 can record corresponding imaging parameters, which are different by sub-volume 24. The receiving and recording is repeated for each sub-volume 24.

At 82, volumetric image data 28 can be reconstructed by the reconstruction unit 26 from the CT projection data and can include tagged sub-volumes 30, e.g. image slices comprising the volumetric image labeled according to imaging parameter changes and/or MonoE image data, e.g. tagged sub-volumes 30 synthesized by energy level. The reconstructing can include synthesizing the reconstructed volumetric image data 28 into the MonoE image data 31. In one embodiment, the reconstruction includes receiving previously reconstructed volumetric image data from storage.

The reference settings 34 selection is received at 84. The selection can be received from the input device 44 and/or as part of other operational information for the CT imaging device 12, such as user login or healthcare practitioner identity, imaging protocol selection, patient information, and the like.

At 86, the volumetric image data, each tagged sub-volume or MonoE image data is mapped according to the selected reference settings, which are adjusted according to a pixel-value distribution analysis. For example, slices in a lower lung region are mapped with a first set of adjusted reference settings. Slices in an upper lung/cardiac region are mapped with a second set of adjusted reference settings. Each mapping includes a linear or non-linear transform of voxel HU values to gray scale values according to the adjusted reference settings.

The one or more mapped sub-volumes, one or more mapped MonoE image data and/or portions of the mapped volume are displayed on the display device 36 at 88. The position and/or orientation of the mapped volume can be determined by commands received from the input device 44.

Figure 6C:
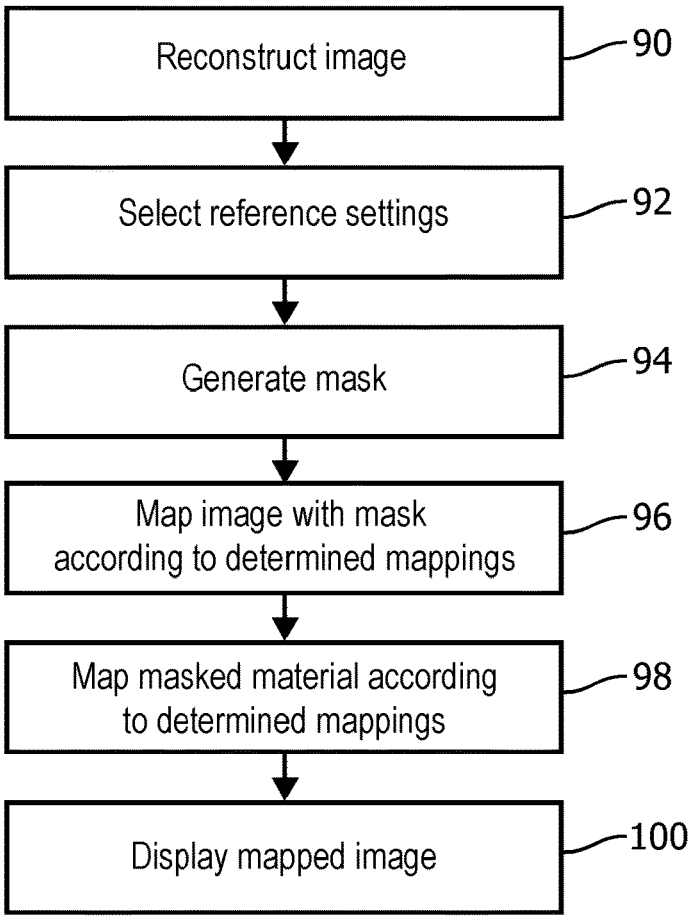

With reference to FIG. 6C, an embodiment of adjusting visualization settings of a CT spectral image is illustrated. At 90, volumetric image data 28 and a material specific image are reconstructed by the reconstruction unit 26 from the spectral projection data.

The reference settings 34 selection is received at 92. The selection can be received from the input device 44 and/or as part of other operational information for the CT imaging device 12, such as user login or healthcare practitioner identity, imaging protocol selection, patient information, and the like.

At 94, a mask 38 is generated for the volumetric image data 28 based on the reconstructed material specific image by the mapping unit 32. The mask is a binary mask, which limits the voxels in the volumetric image data 28 HU values mapped in a first mapping to gray scale values with reference settings or adjusted reference settings.

At 96, the volumetric image data 28 is mapped using the generated mask and according to the first set of selected reference settings or a first set of adjusted reference settings. For example, the volume of an abdominal region is mapped using a mask of iodine_no_water mask. The mapping includes a linear or non-linear transform of HU values to gray scale values selected according to the reference settings or adjusted reference settings.

At 98, the masked material is mapped according to the selected reference settings or adjusted reference settings. For example, the HU values of masked voxels in the abdominal region are mapped to the gray scale values according to the reference settings. The second mapping can be mapped to adjacent gray scale values and/or overlap with the first mapping.

A view of the mapped volume is displayed on the display device 36 at 100. The position and/or orientation of the view of the mapped volume can be determined by commands received from the input device 44 and/or a default according to the imaging protocol.

The above in reference to FIGS. 6A-6C may be implemented by way of computer readable instructions, encoded or embedded on a non-transitory computer readable storage medium, which, when executed by a computer processor(s), cause the processor(s) to carry out the described acts. Additionally or alternatively, at least one of the computer readable instructions is carried by a signal, carrier wave or other transitory medium. Furthermore, the order of the steps can be changed and certain steps can be omitted.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computed tomography (CT) image display system, comprising:
   processor circuitry configured to:
      receive reconstructed volumetric image data of a subject with values in Hounsfield Units (HU), and a set of reference settings;
      adjust the set of reference settings to an adjusted set of reference settings according to a pixel-value distribution analysis of values that are selected from the HU values of the received reconstructed volumetric image data according to the set of reference settings; and
      map the values in HU to gray scale values according to the adjusted set of reference settings; and
   a display device configured to display a view of the received reconstructed volumetric image data according to a linear or non-linear transform of HU values selected according to the adjusted set of reference settings,
   wherein the set of reference settings is according to a first energy level, and the adjusted set of reference settings is according to a second energy level, which is different than the first energy level.

2. The system according to claim 1, wherein the reconstructed volumetric image data includes a plurality of image data, the plurality of image data including at least one of:
   a plurality of image sub-volumes, which include at least one change in imaging parameters; or
   a plurality of Monochromatic Energy (MonoE) image data, which include synthesized image data, each according to a predetermined energy level, and
   wherein each of the plurality of image sub-volumes or each of the plurality of MonoE image data includes a different adjusted set of reference settings.

3. The system according to claim 1, wherein each different adjusted reference settings include an adjusted window level (WL) and an adjusted window width (WW) based on the HU values in the corresponding image sub-volume or MonoE image data selected according to the set of reference settings.

4. The system according to claim 1, wherein the processor circuitry configured to map the HU values in the volumetric image data using at least one mask which eliminates or minimizes masked HU values used in the gray scale mapping according to the adjusted set of reference settings.

5. The system according to claim 3, wherein the adjusted WL is a at least one of a median or a mean of the HU values selected according the reference WL, and the adjusted WW is a function of at least one of a standard deviation, a variance, a kurtosis or a skewness of the HU value distribution selected according to the reference WW.

6. The system according to claim 4, wherein the at least one mask is a mask generated based on a material specific image corresponding to at least one of the reconstructed volumetric image data or one of the image data.

7. The system according to claim 2,
   wherein the processor circuitry is further configured to
      record the imaging parameter changes between sub-volumes of projection data used to reconstruct the volumetric image data.

8. A method of adjusting computed tomography (CT) visualization settings, for received reconstructed volumetric image data of a subject with values in Hounsfield Unit (HU) values and for a received set of reference settings, comprising:
   determining an adjusted set of reference settings from a pixel-value distribution analysis of values that are selected from the HU values of the received reconstructed volumetric image data according to selected reference settings;
   mapping the HU values of voxels, according to the adjusted set of reference settings, to gray scale values; and
   displaying a view of the received reconstructed volumetric image data according to a linear or non-linear transform of HU values selected according to the adjusted set of reference settings,
   wherein the set of reference settings is according to a first energy level, and the adjusted set of reference settings is according to a second energy level, which is different than the first energy level.

9. The method according to claim 8, wherein the reconstructed volumetric image data includes a plurality of image data, the plurality of image data including at least one of:
   a plurality of image sub-volumes, which include at least one change in imaging parameters; or
   a plurality of Monochromatic Energy (MonoE) image data, which include synthesized image data, each according to a predetermined energy level, and
   wherein each of the plurality of image sub-volumes or each of the plurality of MonoE image data include a different adjusted set of reference settings.

10. The method according to claim 8, wherein each different adjusted reference settings include an adjusted window level (WL) and an adjusted window width (WW) based on the HU values in the corresponding image sub-volume or MonoE image data selected according to the set of reference settings.

11. The method according to claim 10, further including mapping the HU values in the volumetric image data using at least one mask which eliminates or weakens masked HU values used in the gray scale mapping to determine the adjusted set of reference settings.

12. The method according to claim 10, wherein the adjusted WL is at least one of a mean or a median of the HU values selected according the reference WL, and the adjusted WW is a function of at least one of a standard deviation, a variance, a kurtosis or a skewness of the HU value distribution selected according to the reference WW.

13. The method according to claim 11, wherein the at least one mask is a binary mask generated based on a material specific image corresponding to at least one of the reconstructed volumetric image or one of the image data.

14. The method according to claim 9, further including:
recording the parameter changes between sub-volumes of projection data used to reconstruct the volumetric image data.

* * * * *